United States Patent [19]

Martini

[11] 4,067,884

[45] Jan. 10, 1978

[54] FLUORINE CONTAINING KETONES

[75] Inventor: Thomas Martini, Neuenhain, Taunus, Germany

[73] Assignee: Hoechst Aktiengesellschaft, Frankfurt am Main, Germany

[21] Appl. No.: 686,032

[22] Filed: May 13, 1976

[30] Foreign Application Priority Data

May 15, 1975 Germany .............................. 2521594

[51] Int. Cl.$^2$ ........................................... C07D 319/10
[52] U.S. Cl. ................................ 260/340.6; 260/594; 219/85 H
[58] Field of Search ..................................... 260/340.6

[56] References Cited

U.S. PATENT DOCUMENTS 2,418,297  4/1947  French et al. ................ 260/340.6 X
3,450,716  6/1969  Selman .......................... 260/340.6 X Primary Examiner—Ethel G. Love
Attorney, Agent, or Firm—Curtis, Morris & Safford

[57] ABSTRACT

By reaction of a perfluoro vinyl ether with a perfluoro carbonic acid fluoride perfluorinated ketones of the formula $R^1-O-CF(CF_3)-CO-R^2$ with at least 13 carbon atoms may be obtained. These ketones may be used as inert solvents of high boiling point. The reaction is catalyzed by cesium fluoride and carried out in an aprotic polar solvent.

13 Claims, No Drawings

FLUORINE CONTAINING KETONES

The present invention relates to novel fluorine containing ketones and to a process for their manufacture.

It is known from U.S. Pat. No. 3,185,734 that highly fluorinated acid fluorides may be converted into fluorinated ketones with hexafluoropropene or perfluoroisobutylene at a temperature from 50° to 250° C in an autoclave in the presence of fluoride ions. This process is advantageously carried out while using polar solvents, for example acetonitrile. It seems however that this reaction cannot be applied to other perfluorinated olefins of low molecular weight.

It is an object of this invention to provide a new process that is substantially more variable than the process of U.S. Pat. No. 3,185,734. It should be possible to perform this process without using an autoclave and to obtain inert perfluorinated organic ketones of high boiling point.

It has now been found that perfluorovinyl ethers of the formula $$R^1 - O - CF = CF^2 \qquad II$$

may be reacted with perfluorinated acid fluorides of the formula $$R^2 - CO - F \qquad III$$

in the presence of cesium fluoride in an aprotic polar solvent at a temperature in the range from −20° to 180° C, perferably from −10° to +150° C, especially from +10° to 80° C.

This reaction is especially surprising as it is known from U.S. Pat. No. 3,257,466 that perfluoro(alkylvinyl)ethers dimerize in the presence of cesium fluoride. Ether containing solvents may moreover be affected in this process while forming undesired by-products. A similar process for the manufacture of ketones is already known from Zh.Vses.Khim.obshch,19(1974),707. In this process high temperatures are however required.

The present invention moreover provides novel perfluorinated compounds of the formula

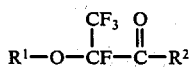

wherein $R^1$ and $R^2$ represent (independent from each other) perfluorinated alkyl groups containing possibly one or several oxygen atoms in ether-like linkage, $R^1$ and $R^2$ having altogether from 10 to 80 carbon atoms. $R^1$ and $R^2$ may be linear, branched or cyclic.

The process is performed according to the following equation:

Compounds wherein $R^1$ and $R^2$ each contain from 6 to 30, preferably from 10 to 25 carbon atoms are used advantageously.

Examples of oxygen-containing radicals $R^1$ are especially perfluoro-2-propoxy-propyl, perfluoro-2,5-dimethyl-3,6-dioxanonyl and perfluoro-2,5,8-trimethyl-3,6,9,-trioxadodecyl.

Among oxygen-containing radicals $R^2$ there by mentioned, by way of example, especially perfluoro-2-propoxy-ethyl, perfluoro-1,4-dimethyl-2,5-dioxaoctyl and perfluoro-1,4,7-trimethyl-2,5,8-trioxaundecyl.

The number of the ether-like bound oxygen atoms optionally contained in the radicals $R^1$ and $R^2$ may amount to half the number of the carbon atoms of the radicals $R^1$ and $R^2$ (when taking into consideration polymers of perfluoroethylene epoxide) or to about one third (when taking into consideration polymers of perfluoropropylene oxide).

As suitable cyclic starting products having several ether-like bound oxygen atoms there may be mentioned, by way of example the following vinyl ethers and acid fluorides which may be derived formally from dioxane:

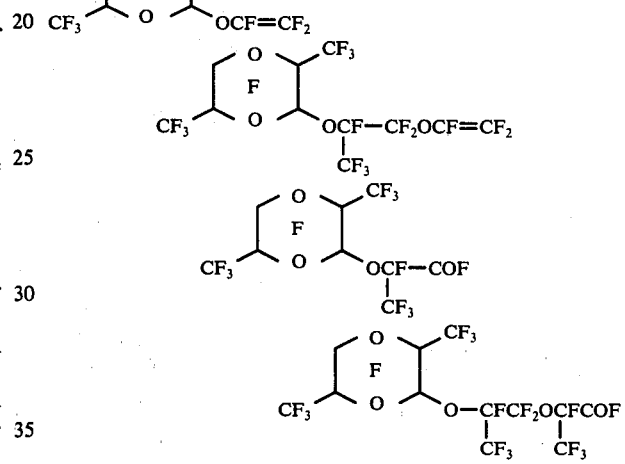

The formula

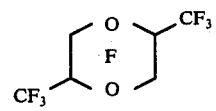

is a shortened form of the formula

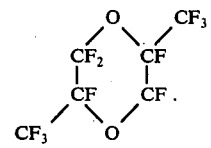

The starting compounds II and III may be obtained by known processes. The vinyl ethers of the formula II, for example, may be prepared from the corresponding perfluoropropionic acid fluorides of the formula

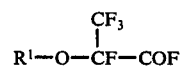

or the alkali metal salts of the corresponding acids, by thermal degradation. The acid fluorides IV may be prepared from hexafluoropropylene epoxide, for example by reacting them with aliphatic perfluorinated carboxylic acid fluorides. The products obtained have the formula

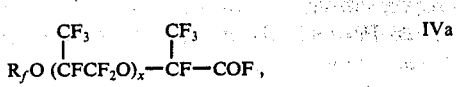

wherein $R_f$ means perfluorinated alkyl preferably having from 1 to 10, especially 3 carbon atoms and $x$ means an integer, preferably from 1 to 20, especially from 1 to 6.

The analogous vinyl ethers of the formula

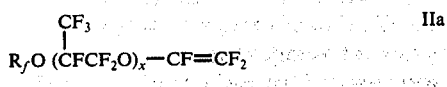

may be prepared thereafter from these acid fluorides. Compounds of the formula IIa as well as of the formula IVa lead to fluoroketones according to the invention which have advantageous properties.

Suitable solvents for the process according to the invention are aprotic polar solvents, for example nitriles such as acrylonitrile, or amides such as dimethylformamide or dimethylacetamide. Alkyl glycol ethers such as dialkyl ethers of glycol, di-, tri- or tetraethylene glycol are preferably used, the alkyl groups of which having from 1 to 2 carbon atoms.

Diethylene glycol dimethyl ether (diglyme) is especially suitable. These solvents are also used together with cesium fluoride in order to polymerize hexafluoropropylene oxide to yield polyethers.

The process according to the invention is generally carried out in the following manner: About equimolar quantities of both reaction components II and III are introduced into a reaction vessel, for example a flask provided with a stirrer, together with the solvent and cesium fluoride. The mixture is stirred at a temperature from $-20°$ to $180°$ C, preferably from $+10°$ to $80°$ C until the reaction is terminated. Instead of cesium fluoride there may also be used rubidium fluoride. An excess of one of the components is possible, but may render difficult the work-up, especially in case of a rather high molecular weight of one of the reaction components.

The reaction is advantageously performed while stirring as intensively as possible. The quantity of the solvent is not critical. It is generally in the range from 10 to 100% of the volume of the mixture of the components II and III.

The quantity of the catalyst is in the range from 1 to 40 g, preferably from 8 to 30 g, especially from 12 to 20 g per 100 g of the compound III. Greater quantities are possible, but do not bring about any advantages.

In its reactive form the catalyst is dissolved in the solvent. This catalyst solution may be readily separated (with the latter) from the perfluorinated reaction products precipitating in the form of an insoluble oil. An especial advantage of the process according to the invention resides in the fact that this catalyst solution may be used repeatedly for further reactions.

The end of the reaction may be readily observed by means of IR spectroscopy. The reaction is performed until the intensive absorption signal of the acid fluoride group (about 5.3 $\mu$) or of the vinyl ether group (about 5.5 $\mu$) has practically disappeared and until the carbonyl band of the ketone (5.6 $\mu$) appears.

The products according to the invention of the formula I represent a class of neutral, inert perfluorinated compounds. They do not react with $SF_4$ or $UF_6$. They are moreover stable towards acids and oxidants. Inert liquids having a boiling point in the range from about 100° to 500° C may be prepared according to the process of the invention, depending on the chosen reaction components of the formulae II and I, which liquids may be used as heat transfer agents when having a low molecular weight and as lubricants when having a high molecular weight. An advantage of the process of the invention resides in the fact that it enables preparing a homogeneous final product by using as starting products homogeneous compounds even of high molecular weight. In the known polymerization of hexafluoropropene epoxide or tetrafluoroethylene epoxide on the contrary there is always obtained a number of products having a different degree of polymerization. This uniformity will be desirable in most cases, for example when using heat transfer agents for soldering processes. This process designated as "Condensation Soldering" has been presented to the public in 1974 (R. C. Pfahl, J. C. Mollendorf, T. Y. Chu, NEPCON West, 1974).

According to this process a liquid having a high boiling point is heated to the boil. When plunging an object into the saturated vapor, the latter condenses, whereby the object is rapidly heated to the boiling point of the liquid. The higher the molecular weight of the liquid the higher the density of its vapor. The boiling point of the liquid is chosen so that the desired metal parts, for example superposed printed circuits melt. On the other hand sensitive spots must not be damaged chemically. The liquid must be noncombustible, chemically and thermally inert and nontoxic. For junctions provided with an alloy having a melting point of 183° C (60% of tin, 40% of lead) fluorinated polyoxypropylenes, for example, have been proposed (molar weight 950, boiling point 224° C).

The products of the formula I may also be used for this process. They are chemically and thermally stable; in this case the boiling point of the liquid may be adjusted to the melting point of the corresponding metal by varying the radicals $R^1$ and $R^2$.

When using as starting compounds vinyl ethers and acid fluorides having about the same molecular weight there is obtained a product having about the double molecular weight of the reactants owing to the fact that the process of the invention constitutes an addition reaction. The same fact applies when using high molecular weight starting compounds, for example a polymer of hexafluoropropene oxide. These compounds still contain a terminal acid fluoride group which may be converted into a vinyl group in known manner. The vinyl ether obtained in this way is reacted with the originally used acid fluoride. Perfluorinated ethers having a molecular weight of up to about 4500 may thus be prepared by reacting said high molecular weight acid fluorides — readily obtainable from a perfluorinated epoxide — with the analogous vinyl ethers, with especially good yields up to a molecular weight of about 3000.

The following oligomers may be used especially as feed products having a defined molecular weight:

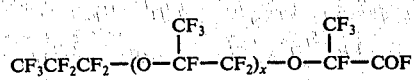

wherein $x$ is an integer from 1 to 6, preferably from 2 to 4, as well as

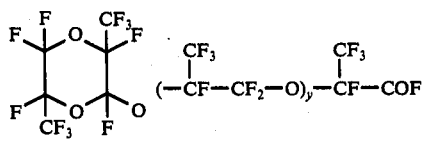

wherein y is an integer from 0 to 5, preferably from 1 to 3.

The latter compounds wherein y is 0 or 1 may be readily obtained from hexafluoropropylene epoxide. The compounds wherein y is an integer from 2 to 5 may be obtained from the compounds wherein y is 0 or 1 by the known addition of hexafluoropropene oxide to acid fluorides in the presence of cesium fluoride in aprotic polar solvents.

The following examples illustrate the invention:

EXAMPLE 1

Perfluoro-2,4-bis(3',6'-dimethyl-1',4'-dioxane-2'-oxy)-pentanone-3

100 ml of diglyme and 40 g of CsF were introduced into a three-necked flask provided with a reflux condenser, a stirrer and a thermometer and 476 g (1.0 mol) of perfluoro-[α-(3,6-dimethyl-1,4-dioxanyl-2-oxy)-propionic acid fluoride] were added thereto. The mixture was stirred for 2 hours at room temperature and 410 g (1.0 mol) of perfluoro-3.6-dimethyl-1.4-dioxanyl-2-vinyl ether were slowly added dropwise. The mixture was thereafter stirred for 1 week at 30° C, both phases were separated from one another and the lower phase was distilled. 690 g (78.8% of the theory) of the compound

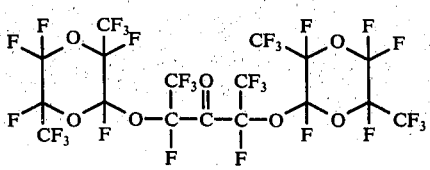

$C_{17}F_{30}O_7$ molecular weight 886 were obtained, having a boiling point of from 219° to 221° C.

Analysis: Calculated: C 23.0%; F 64.3%. Found: C 22.9%; F 63.6%.

The structure could be confirmed by IR, NMR and mass spectra.

EXAMPLE 2

Into the three-necked flask of Example 1 there was introduced the upper phase separated in Example 1 and 476 g of perfluoro[α-(3.6-dimethyl-1.4-dioxanyl-2-oxy)-propionic acid fluoride] were added. The further procedure was as in Example 1. After having worked up the mixture 772 g (87.1% of the theory) of the product of Example 1 were obtained.

EXAMPLE 3

Perfluoro-[di-(1,4-dimethyl-2,5-dioxa-5-(3',6'-dimethyl-1',4'-dioxane-2-yl)-pentyl)-ketone]

In an analogous manner to Example 1 224 g (0.349 mol) of perfluoro[2,5-dimethyl-3-oxa-5-(3',6'-diethyl-1,4-dioxane-2-yl-oxy)]-valeric acid fluoride were added to 30 g of CsF and 60 ml of diglyme at 25° C and the mixture obtained was stirred for one hour. 200 g of perfluoro-α-(3.6-dimethyl-1.4-dioxanyl-2-oxy)-propyl-vinyl ether (0.347 mol) were added. The mixture was stirred for 48 hours at 40° C. By distillation of the precipitating heavier phase there were obtained 249.5 g (59.2% of the theory) of the ketone of the formula

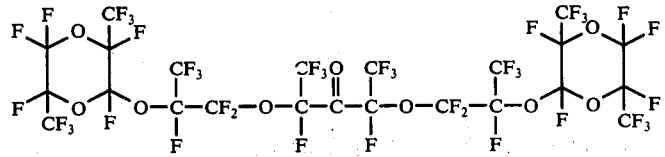

$C_{23}F_{42}O_9$; molecular weight; 1218 boiling point from 105° to 107° C/0.4 torr Analysis: Calculated: C 22.6%; F 65.6%. Found: C 22.6%; F 64.7%.

EXAMPLE 4

Perfluoro-di-(5-methyl-3,6-dioxanonyl-2)-ketone 498 g (1 mol) of perfluoro-[α-(2-n-propoxy-propoxy)-propionic acid fluoride] were added to 60 g of CsF and 150 ml of diglyme at 25° C, the mixture was stirred at room temperature for one hour and intensively mixed after having added 403 g (0.932 mol) of perfluoro-2-n-propoxypropylvinyl ether at 40° C. The precipitating heavier phase was separated and distilled. 615 g (70.9% of the theory) of ketone were obtained having the formula

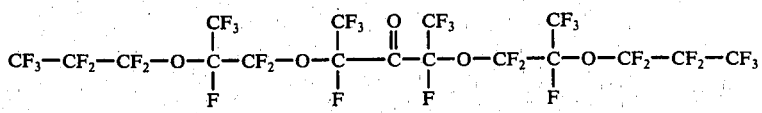

$C_{17}F_{34}O_5$ molecular weight 930; boiling point 61° C/0.3 torr (from 219° to 220° C/760 torr)

Analysis: Calculated: C 21.95%; F 69.5%. Found: C 21.8%; F 69.0%.

EXAMPLE 5

Perfluoro-5,7,10-trimethyl-4,8,11-trioxa-tetradecanone-6

180 g (0.361 mol) of perfluoro-[α-2-n-propoxy-propoxy)-propionic acid fluoride] were added to 40 g of CsF and 100 ml of diglyme and the mixture was stirred for 2 hours. 96 g of perfluoropropylvinyl ether (0.361 mol) were slowly added and the mixture was stirred at 30° C for 6 days. The separated heavier phase was distilled and 149.5 g (53.2% of the theory) of ketone were obtained having the formula

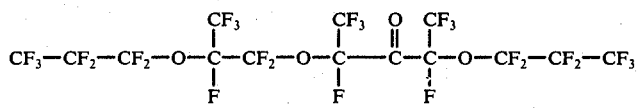

$C_{14}F_{28}O_4$ molecular weight 764; boiling point from 180° to 185° C

Analysis: Calculated: C 22.0%; F 69.6%. Found: C 21.8%; F 68.5%.

The structure could be confirmed by IR, NMR and mass spectra.

EXAMPLE 6

30 g of CsF in 80 ml of diglyme were added to 192 g of a vinyl ether of a hexafluoropropene epoxide polymer having a boiling point of from 80° to 175° C/0.3 torr and an average molecular weight of 1700. This vinyl ether had been prepared by fractionated distillation of a polymer mixture resulting from the polymerization of hexafluoropropene epoxide with CsF, and subsequent conversion of the terminal acid fluoride group into a vinyl ether group. 145 g of perfluoro-α-(3,6-dimethyl-1,4-dioxanyl-2-oxy-)-propionic acid fluoride were added and the reaction mixture was stirred for 52 hours at 60° C. The precipitating heavier phase was distilled to yield 200 g of an oil having a boiling point from 100° to 240° C/0.3 torr.

According to the IR spectrum the vinyl ether had been completely converted into the β-carbonyl ether compound (C=C absorption at 5.5 μ disappeared in favor of the C=O absorption at 5.7 82 ).

EXAMPLE 7

Saturation of the terminal group of a hexafluoropropene epoxide polymer 100 g of a hexafluoropropene epoxide polymer having an average molecular weight of 1300, a boiling point from 85 to 107° C/1 torr, which had been prepared in an analogous manner to Example 2 of German Offenlegungsschrift No. 24 51 493, and contained consequently two terminal perfluoroisopropionic acid fluoride groups, were dissolved with stirring in 70 ml of diglyme. 30 g of CsF and 200 g of perfluoro-3,6-dimethyl-1,4-dioxanyl-2-vinyl ether were added and the reaction mixture was stirred for 55 hours at 60° C.

The heavy phase was separated and distilled thereafter. Besides a first fraction of 43 l g (boiling point from 48 to 90° C/0.05 torr) there was obtained as main quantity 120 g of a polymer substance having a boiling point from 93° to 138° C/0.09 torr, wherein acid fluoride groups (5.32 μ) could not be detected by IR spectroscopic determination, whereas a band to be attributed to the β-carbonyl ether group (C=O) appeared at 5.62 μ.

EXAMPLE 8

From a hexafluoropropene epoxide polymer having an acid fluoride terminal group (average molar weight 1500, boiling point from 130° to 195° C/0.1 torr) there was obtained the free acid by hydrolysis, which acid was used to prepare the potassium salt. By pyrolyzing the potassium salt in known manner the corresponding perfluorovinyl ether was obtained (boiling point from 123° to 170° C/0.1 torr average molar weight 1434). 120 g of the acid fluoride used as well as 80 ml of diglyme and 30 g of cesium fluoride were added to 150 g of the vinyl ether mixture obtained. The reaction mixture was stirred for 56 hours at 60° C. Thereafter the intensive acid fluoride band in the IR spectrum (5.32 μ) had completely disappeared in favor of the C=O absorption of the β-carbonyl ether group (5.62 μ).

The product mixture was diluted with 300 ml of trifluorotrichloroethane, admixed with 500 ml of water and well shaken to remove diglyme. The precipitating heavier phase was distilled. After elimination of trifluorotrichloroethane there were obtained 80 g of a fraction having a boiling point from 130° to 200° C/0.1 torr (which contained an excess of vinyl ether used) and 160 g of a fraction having a boiling point from 200° to 270° C/0.1 torr.

EXAMPLE 9

Perfluoro-(2-propoxy-pentanone-3)

133 g of perfluoropropylvinyl ether, 30 g of CsF and 80 ml of diglyme were introduced into an autoclave provided with a shaking device and 83 g of perfluoropropionic acid fluoride were incorporated by condensation. The mixture obtained was stirred for 48 hours at 40° C. The treatment of the reaction mixture yielded 124 g of the above mentioned ketone having a boiling point from 92° to 94° C (yield of 57.5% of the theory). The structure could be confirmed by $^{19}$F-NMR, IR and mass spectra and by C/F- analysis.

Analysis: Calculated: C 22.9%; F 70.4%. Found: C 22.3%; F 70.2%.

EXAMPLE 10

Perfluoro-3,6-dimethyl-1,4-dioxanyl-2-vinyl-ether 2800 g of a mixture of hexafluoropropene epoxide and hexafluoropropene (in a weight ratio of 65:35) were introduced into a solution of 600 ml of diethylene glycol dimethyl ether and 600 g of $PO[N(CH_3)_2]_3$ in a three-necked flask provided with an intensive condenser, a stirrer and a thermometer for low temperatures, at a temperature from −40° to −30° C while continuously stirring, at a rate of 40 l/h (measured under normal conditions of temperature and pressure, i.e. at 0° C and under 760 mmHg).

Thereafter the reaction mixture was stirred for 5 hours at the above mentioned temperature. By slowly heating to 0° C hexafluoropropene and the excess of epoxide were expelled and the two phase mixture was separated in the separation funnel. The lower phase (1742 g) was washed with 600 ml of acrylonitrile and yielded 1554 g of product mixture from which 1142 g of a substance boiling at a temperature from 115° to 118° C and 194 g of a second fraction boiling at a temperature from 118° and to 170° C could be obtained by fractional distillation, the first one having the formula

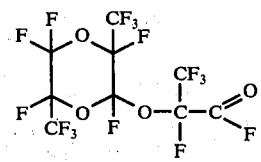

according to elementary, IR and NMR -spectroscopic analyses and representing the hitherto unknown perfluoro-[α-3,6-dimethyl-1,4-dioxanyl-2-oxy]-propionic acid fluoride.

794 g (1.67 mol) of this substance were added dropwise to 160 ml of water while cooling with ice and stirring. The mixture obtained was then neutralized with 20% KOH solution and concentrated at the rotation evaporator. The material thus predried was kept on a sheet in a vacuum drying oven for 24 hours at 100° C under 300 torrs, ground to fine particles and again heated for the same period to 100° C under 0.1 torr.

The dry product obtained was heated for 30 hours to a temperature from 200° to 225° C in a vacuum of from 5 to 0.1 torr in a 2 liter round-bottomed flask being connected with two following cold traps. The collected pyrolysate (628 g) was distilled by fractionation.

After a first fraction of 8 g (boiling point from 97° to 103° C) there were obtained 584 g (85.2% of the theory) of perfluoro-3,6-dimethyl-1,4-dioxanyl-2-vinyl ether having a boiling point from 103° to 106° C.

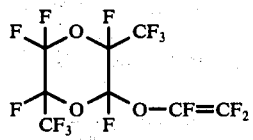

$C_8F_{14}O_3$ molecular weight 410

Analysis: Calculated: C 23.4%; F 64.9%, Found: C 23.6%; F 65.2%,

Ir and $^{19}$—F—NMR spectra confirmed the structure. A strong band appeared at 9.65 μ in the IR spectrum. Distilling residue: 32 g.

EXAMPLE 11

Perfluoro-[α-(3,6-dimethyl-1.4-dioxanyl-2-oxy-propyl)-vinyl ether]

From the second fraction having a boiling point from 118° to 170° C which had been obtained in the preparation of perfluoro-[α-(3,6-dimethyl-1,4-dioxanyl-2-oxy)]-propionic acid fluoride according to Example 1 there were obtained 67% by weight of a compound having a boiling point in the range from 160° to 164° C by a further fractional distillation, which compound corresponded to the formula

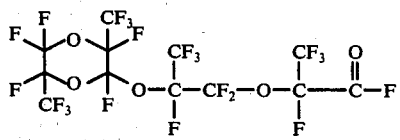

$C_{12}F_{22}O_5$ molecular weight 642 according to the elementary, IR and NMR -spectroscopic analyses and represented the hitherto unknown perfluoro-[α-(3.6-dimethyl-1,4-dioxanyl-2-oxypropoxy)]-propionic acid fluoride.

623 g (0.97 mol) of this acid fluoride were introduced dropwise into 100 ml of water while cooling with ice. The reaction mixture was then neutralized with 10% KOH and concentrated at the rotation evaporator. The predried material was then kept for 15 hours at a temperature of 100° C/300 torrs and dried thereafter for 62 hours at a temperature of 100° C/0.1 torr. Then it was heated to 200° C under a pressure from 5 to 0.1 torrs for 24 hours.

By distilling the pyrolysate obtained in analogous manner to Example 1 346 g (61.9% of the theory) of a vinyl ether were obtained having a boiling point from 151° to 154° C and corresponding to the structure

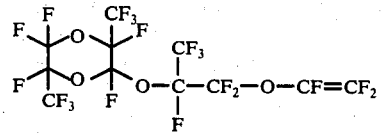

$C_{11}F_{20}O_4$ molecular weight 576

Analysis: Calculated: C 22.9%; F 65.9%. Found: C 22.8%; F 65.5%.

according to the NMR, IR and mass spectrometry as well as to the elementary analysis.

What is claimed is:

1. Perfluorinated ketones of the formula

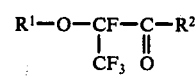

wherein $R^1$ and $R^2$ may be the same or different and each is a perfluorinated alkyl group that may contain one or more ether oxygen linkages, $R^1$ and $R^2$ having a total of 10 to 80 carbon atoms, and at least one of said perfluorinated alkyl groups being a cyclic alkyl group having a 6-membered ring with oxygen atoms in the 1 and 4 position thereof.

2. Compounds as claimed in claim 1, wherein $R^1$ means

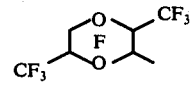

or

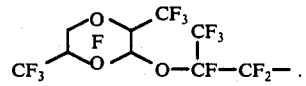

3. Compounds as claimed in claim 1, wherein $R^1$ means the radical

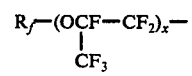

wherein x is an integer from 1 to 20 and $R_f$ means perfluorinated alkyl having from 1 to 10 carbon atoms.

4. Compounds as claimed in claim 1, wherein $R^2$ means

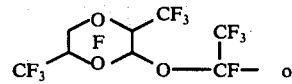

or

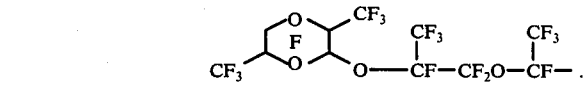

5. Compounds as claimed in claim 1, wherein $R^2$ means the radical

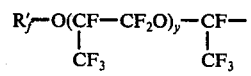

wherein $y$ is an integer from 1 to 20 and $R'_f$ means perfluorinated alkyl having from 1 to 10 carbon atoms.

6. Compounds as claimed in claim 1, wherein $R^1$ and $R^2$ have a total of 14 to 60 carbon atoms.

7. Compounds as claimed in claim 1, wherein $R^1$ and $R^2$ each contain from 6 to 30 carbon atoms.

8. Compounds as claimed in claim 7, wherein $R^1$ and $R^2$ each contain from 10 to 25 carbon atoms.

9. A compound having the formula

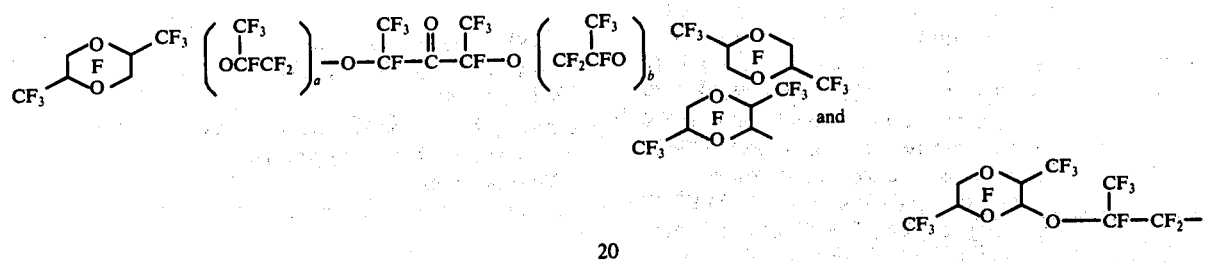

wherein $a$ and $b$ may be the same or different and are 0 or 1.

10. Compounds as claimed in claim 5 having the formula

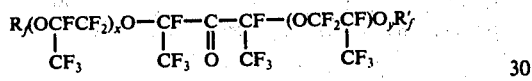

wherein $R_f$ and $R'_f$ may be the same or different and are perfluorinated alkyl radicals having from 1 to 10 carbon atoms, $x$ and $y$ are integers of 1 to 20, and the sum of $x$ and $y$ is 2 to 24.

11. Compounds as claimed in claim 6 having the formula

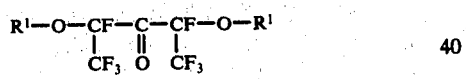

wherein $R^1$ has from 6 to 29 carbon atoms.

12. A perfluorinated ketone of the formula

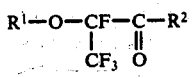

wherein $R^1$ is selected from

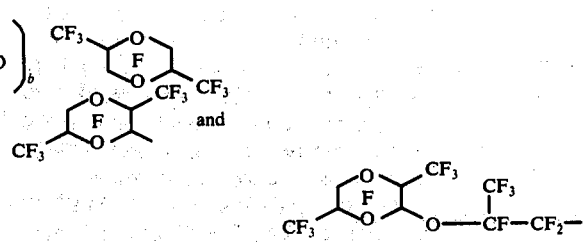

$R^2$ is a linear, branched or cyclic perfluorinated alkyl radical that may contain one or more ether oxygen linkages and $R^1$ and $R^2$ have a total of 10 to 80 carbon atoms.

13. A perfluorinated ketone of the formula

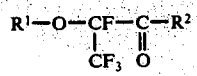

wherein $R^1$ is a linear, branched or cyclic perfluorinated alkyl radical that may contain one or more ether oxygen linkages, $R^2$ is

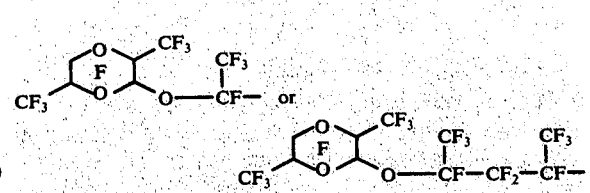

and $R^1$ and $R^2$ have a total of 10 to 80 carbon atoms.

* * * * *